United States Patent [19]
Dror et al.

[11] Patent Number: 5,807,471
[45] Date of Patent: Sep. 15, 1998

[54] SENSOR FOR DETECTING LOW CONCENTRATIONS OF POLYIONS

[75] Inventors: Michael Dror; Robert F. Baugh, both of Parker; Peter Ross Schaad, Aurora, all of Colo.

[73] Assignee: Medtronic, Inc., Minneapolis, Minn.

[21] Appl. No.: 640,274

[22] Filed: Apr. 30, 1996

[51] Int. Cl.⁶ .................................................. G01N 27/26
[52] U.S. Cl. ...................... 204/418; 204/403; 435/287.1; 435/817; 422/82.03
[58] Field of Search ..................................... 204/418, 415, 204/403; 435/817, 287.1; 422/82.02

[56] References Cited

U.S. PATENT DOCUMENTS

| | | | |
|---|---|---|---|
| 4,806,393 | 2/1989 | Levin | 427/384 |
| 5,209,931 | 5/1993 | Levin | 424/405 |
| 5,236,570 | 8/1993 | Ma et al. | 204/418 |
| 5,415,746 | 5/1995 | Cha | 204/418 |
| 5,453,171 | 9/1995 | Ma et al. | 204/418 |

*Primary Examiner*—Bruce F. Bell

[57] ABSTRACT

A ion selective electrode is formed by an electrode having a first membrane with a diffusion rate selective to heparin or other polyions, and a selective polymeric coating thereon having a polyion diffusion rate lower than the polyion diffusion rate of the first membrane. The electrode is sensitive to solutions containing low polyion concentrations such as low heparin concentrations.

20 Claims, 2 Drawing Sheets

SENSOR FOR DETECTING LOW CONCENTRATIONS OF POLYIONS

BACKGROUND OF THE INVENTION

1. Field of the Invention

The present invention relates to organic membrane type ion selective electrodes. More specifically, the present invention relates to polymer membrane type polyion selective electrodes suitable for monitoring polymeric polyion macromolecules such as the polysaccharide heparin.

2. Brief Description of the Prior Art

Anion exchange selective polymeric membranes which are specific for ionic macromolecules, specifically heparin, are disclosed in U.S. Pat. No. 5,236,570, issued Aug. 17, 1993, and U.S. Pat. No. 5,453,171, issued Sep. 26, 1995. Both of these patents disclose heparin selective membranes formed of a polymeric material, a plasticizer and a quaternary ammonium chloride such as tridodecyl methyl ammonium chloride. A membrane is formed and mounted on the end of an electrode tube inserted in a sample solution such as blood containing unknown amounts of heparin. The potentiometric response between the membrane electrode and a reference electrode is a function of the concentration of heparin ions in the sample solution. The concentration is determined by reference to a standard curve established by measuring the EMF of solutions of known heparin concentrations.

Cross-linkable substituted polyvinyl chlorides are disclosed in U.S. Pat. No. 4,806,393. The PVC disclosed is produced as the reaction product of, for example, sodium diethyl dithiocarbamate and polyvinyl chloride.

OBJECTS OF THE INVENTION

It is the principal object of the present invention to detect and quantitatively measure low concentrations of polyions such as heparin in blood samples or other solutions.

Another object of the present invention is to increase the accuracy of the polyion detection in highly dilute solutions containing only very minute amounts of polyion.

A further object of the present invention is to facilitate the production of smaller polyion detection devices.

SUMMARY OF THE INVENTION

In accordance with the foregoing objects, a polyion selective electrode is formed by an electrode tube having opposite ends with a silver/silver chloride (Ag/AgCl) electrode inserted into said tube from one end thereof. A polyion-selective membrane closes the other end. In order to facilitate detection of polyions such as heparin in lower concentrations, a polyion-selective polymeric coating is applied over the opposite end of the tube and membrane, the polymeric coating has a dense morphology, thus having a polyion diffusion rate lower than the polyion diffusion rate of the membrane.

The polymeric coating is preferably a cross-linkable polymer such as thiocarbamate-substituted polyvinyl chloride, produced as the reaction product of a sodium dialkyl dithiocarbamate and polyvinyl chloride, with added amounts of a quaternary ammonium chloride salt such as tridodecyl methyl ammonium chloride. No plasticizer is used, thereby providing a denser layer compared to the membrane.

DESCRIPTION OF THE PREFERRED EMBODIMENT

Figure 1:
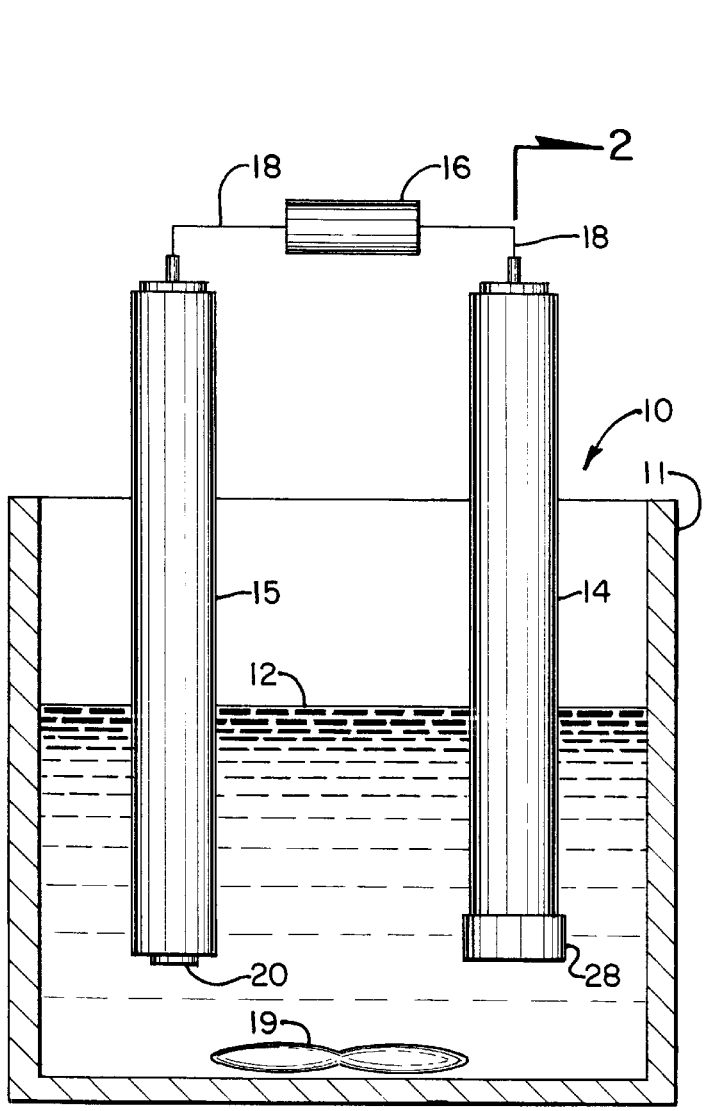
FIG. 1 is a schematic view of a heparin detection potentiometric circuit including a heparin detection electrode, a potentiometer and a reference electrode, the electrodes being inserted in a solution in a container.

The present invention is embodied in a test cell 10 formed by a container 11 containing a blood or polyion solution 12, such as a heparin solution, to be tested. A polyion-sensitive electrode 14 and a reference electrode 15 are inserted into the blood or polyion solution bath such as a heparin solution bath. The electrodes are connected in series with a potentiometer 16, such as a pH meter, by appropriate wires or conductors 18. A magnetic stirrer 19 in the bottom of the container stirs and circulates the blood or polyion solution. An alternative mode of testing involves immersing electrodes 14, 15 in a nonstirred solution (see FIG. 1).

The reference electrode 15 may be of any appropriate construction such as a calomel or double junction silver/silver chloride (Ag/AgCl) reference electrode. The reference electrode is also inserted in the blood or polyion solution and connected to the potentiometer.

Figure 2:
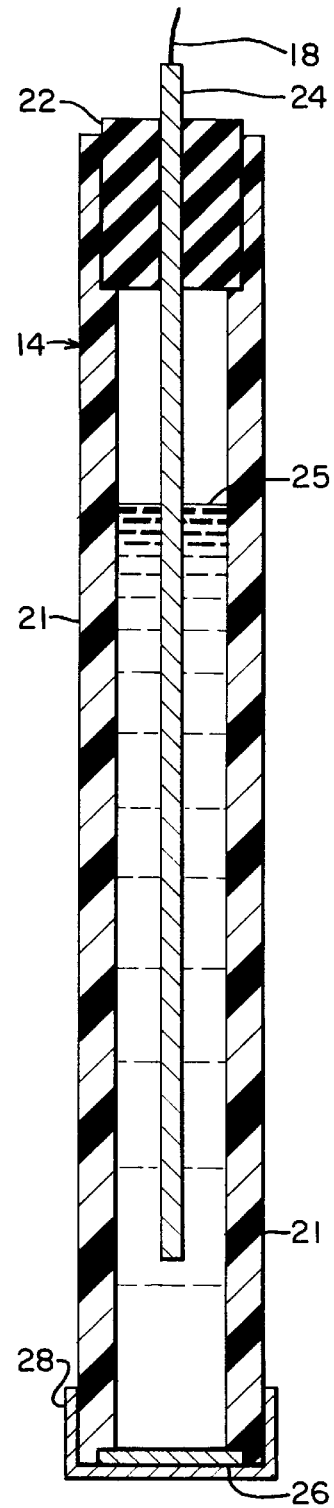
FIG. 2 is an enlarged section view taken substantially in the plane of line 2—2 on FIG. 1.

The polyion sensor electrode 14, as shown in cross-section in FIG. 2, is formed by an elongated tubular housing 21 formed of polyvinyl chloride or like impervious material. At its upper end the tube 21 supports a cap 22 which in turn carries an elongated silver/silver chloride (Ag/AgCl) wire 24 inserted into a sodium chloride solution 25 contained within the tubular housing 21.

In accordance with the present invention, the lower end of the polyion sensor electrode tube 21 is closed by a primary polyion selective polymer membrane 26. An outer thin cross-linked polyion selective polymer membrane 28 covers the lower end of the tube and the primary polyion selective membrane 26 for purposes of reducing the rate of diffusion of polyion molecules and thereby enabling the sensor to sense and measure lower solution concentrations of polyion.

The primary heparin selective membrane is prepared according to U.S. Pat. Nos. 5,236,570 and 5,453,171 and is selective to heparin. The presence of heparin in the solution 12 creates an electromotive force across the heparin selective membrane which EMF is measured and indicated by the potentiometer 16 in the electrical circuit formed by the heparin solution, electrodes 14, 15, connector 18 and potentiometer 16. The voltage or EMF indicated by the potentiometer 16 is a function of the concentration of heparin in the blood or polyion solution 12.

In order to increase the sensitivity of the primary membrane 26 and thereby enable the test cell to sense the heparin content of solutions of lower heparin content, a further heparin sensitive membrane is applied as a thin cross-linked membrane coating over the primary membrane and bottom end of the heparin sensor electrode tube 21, as shown in FIG. 2. The outer polymer coating composition has a heparin diffusion rate or constant which is less than the heparin diffusion rate of the membrane, thereby increasing the sensitivity of the test cell. To this end, an outer, rigid, thin heparin selective membrane is formed, e.g., from a cross-linkable polymer such as thiocarbamate-substituted polyvinyl chloride, described in U.S. Pat. No. 4,806,393, containing an appropriate quaternary ammonium compound, such as tridodecyl methyl ammonium chloride, and preferably without a plasticizer so that it provides a dense, relatively rigid membrane layer as compared to the inner membrane 26.

More specifically, the cross-linkable polyvinyl chloride is produced as the reaction product of dibutyl dithiocarbamate and polyvinyl chloride. The coating is applied by dipping the tube 21 and membrane 26 into a solution of the cross-linkable polyvinyl chloride in tetrahydrofuran solvent and allowing the coating to dry and cross-link. The coating thickness may be increased by repeated dips and drying. Cross-linking of the coating may be effected or accelerated by exposure to heat or light.

Other equally effective outer coatings may be prepared from cross-linkable polymeric compounds such as other substituted polyvinyl chloride compounds. Generally, cross-linkability can be provided by substituents containing double bonds characterized by the formula $-C_nH_{2n}-$, including $-C_nH_{2n}-CH=CH_2$, as well as by mercaptan and sulphyaryl groups, appropriate silicon groups, plasma polymerized thin films, or by radiation of polymers such as polyvinyl chloride with gamma radiation.

Other useful quaternary ammonium salts are disclosed in U.S. Pat. Nos. 5,236,570 and 5,453,171 and include, among others, trimethyl phenyl ammonium chloride, dimethyl diocladecyl ammonium bromide, and polybrene.

If desired, a plurality of dip coating solutions can be prepared with varying amounts of plasticizer in the coating solutions to provide a transition gradient across the tube coating 28. Useful plasticizers are disclosed in U.S. Pat. Nos. 5,236,570 and 5,453,171 and include, among others, dioctyl sebacate, isopropyl palmitate, and isopropyl isostearate.

The following illustrative examples will illustrate the present invention.

EXAMPLE 1

A polyvinyl chloride hard plastic tube having a 0.244 inch outer diameter, a 0.154 inch inner diameter, and approximately 3.9 inches in length was provided at one end with a heparin sensitive membrane. The membrane had a composition of 33% by weight of the plasticizer dioctyl sebacate, 2% by weight of the quaternary ammonium salt tridodecyl methyl ammonium chloride, and 65% by weight polyvinyl chloride, and was formed to a thickness of 0.01 inch. The membrane was prepared by dissolving all components in the solvent tetrahydrofuran in the appropriate proportions and cast as a film on a glass plate. After drying, a circular piece of 0.197 inch diameter was cut from the membrane and solvent glued to the end of the tube using tetrahydrofuran as the solvent to effect adequate adhesion.

EXAMPLE 2

The membrane end of a tube and membrane prepared according to EXAMPLE 1 was coated with coating solution containing 5% by weight of the cross-linkable thiocarbamate-substituted polyvinyl chloride polymer produced as the reaction product of sodium dibutyl dithiocarbamate and polyvinyl chloride, dissolved in tetrahydrofuran solvent, and containing tridodecyl methyl ammonium chloride therein at 0.1% by weight, and without a plasticizer. The coating was completed by very briefly dipping the heparin sensor in the polymer and quaternary ammonium salt solution to a depth of about 0.05 inch to provide a thin layer, cross-linkable polyvinyl chloride coating thereon. The tube was immediately removed from the coating solution and dried. The dipping was repeated to form a thin layer of the cross-linkable polymer on the end of the sensor, providing a cross-linked coating in the range of 0.0001 inch to 0.001 inch in thickness.

Figure 3:
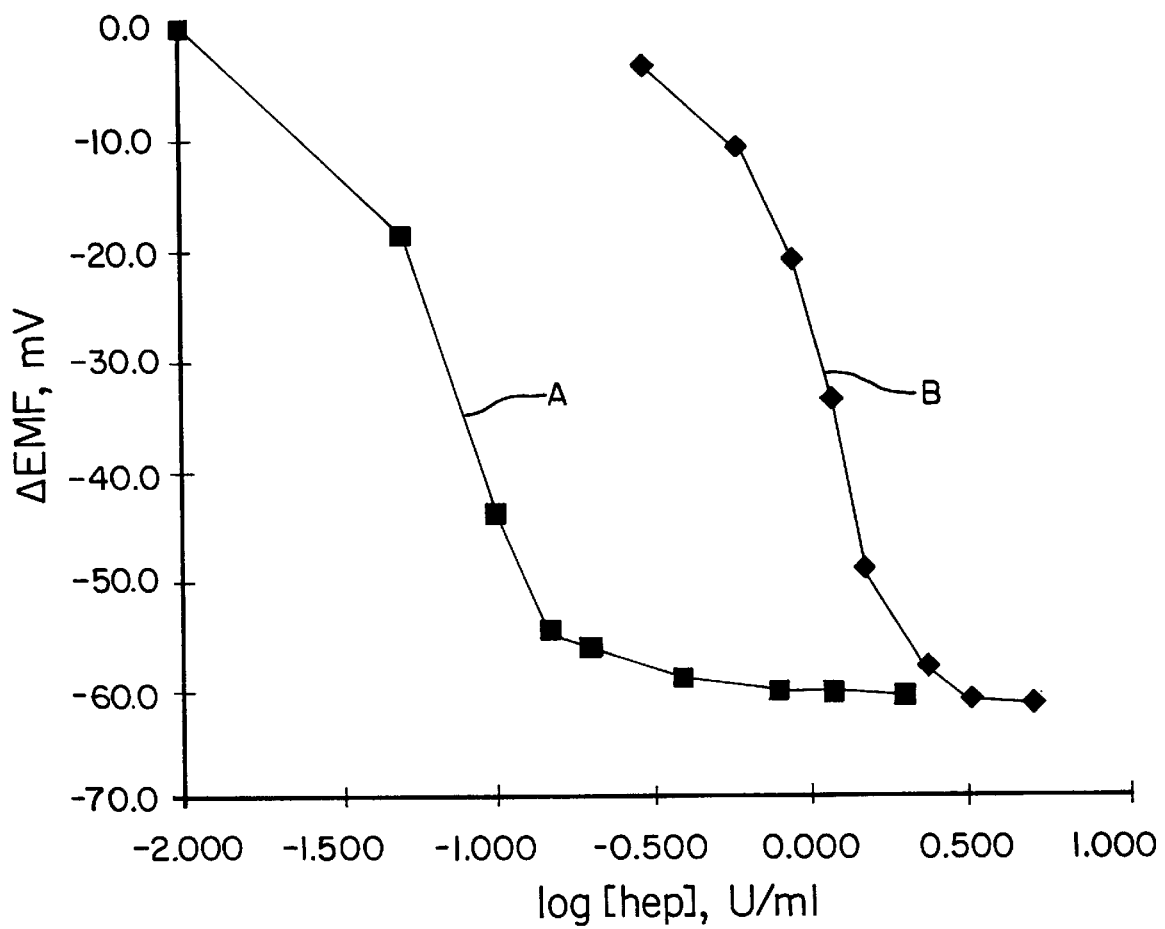
FIG. 3 shows plots of EMF measurements in mV for a series of standard heparin solutions using a sensor embodying the present invention (Curve A) and a standard sensor (Curve B).

A heparin sensor electrode prepared according to EXAMPLE 2 was used to prepare a standard curve of heparin concentrations. A typical response curve using the sensor embodying the present invention is shown as Curve A in FIG. 3. This curve was obtained by immersing the sensor 14 in a series of standard heparin solutions of different concentrations, in 0.12M NaCl, and determining the EMF in mV from the potentiometer 16. After being exposed to each standard heparin solution, the sensor 14 was immersed in 2M NaCl for three minutes before immersing in the next standard solution.

A solution containing an unknown heparin concentration may be analyzed for its heparin content by utilizing a heparin sensor electrode as described in EXAMPLE 2 in a test cell containing a heparin solution. The EMF of the solution with unknown heparin content is measured, and by referring to a calibration curve prepared as described, the heparin content can be readily determined.

In a second approach, a known quantity of protamine is titrated with aliquots of an unknown solution of heparin. A sensor prepared according to EXAMPLE 2 can be employed for detecting the titration endpoint. For measurements in blood or plasma, the sample can be anticoagulated with EDTA or citrate. This procedure provides a means for determining the heparin concentration without resorting to using a coagulation endpoint. To this end, aliquots of a solution with an unknown heparin concentration are gradually added to a stirred solution of a known amount of protamine, and the resulting EMF values are plotted, from which the unknown heparin concentration can then be determined by the intersection of the slopes of the curve. The titration can also be carried out in the reverse sequence, in which increasing amounts of protamine are added to a series of samples of the unknown solution of heparin. The latter approach is especially suitable for testing of blood.

While a certain illustrative embodiment of the present invention has been described above in considerable detail, it should be understood that there is no intention to limit the invention to the specific embodiment disclosed. On the contrary, the intention is to cover all modifications, alternatives, equivalents and uses falling within the spirit and scope of the invention as expressed in the appended claims.

We claim:

1. An ion-selective electrode comprising an electrode membrane selective to heparin and having a heparin diffusion rate, and a heparin-selective crossed-linked polymeric coating thereon having a heparin diffusion rate lower than the heparin diffusion rate of said heparin selective membrane.

2. An ion-selective electrode as defined in claim 1 wherein said polymeric coating comprises a thiocarbamate substituted polyvinyl chloride.

3. An ion-selective electrode as defined in claim 1 wherein said polymeric coating comprises the reaction product of sodium dibutyl dithiocarbamate and polyvinyl chloride.

4. An ion-selective electrode as defined in claim 3 wherein said polymeric coating further comprises sodium dibutyl dithiocarbamate and polyvinyl chloride and a quaternary ammonium salt.

5. An ion-selective electrode of claim 1, wherein said heparin-selective cross-linked polymeric coating comprises a substituted polyvinyl chloride.

6. An ion-selective electrode of claim 1, wherein said heparin-selective cross-linked polymeric coating is substantially free of a plasticizer.

7. An ion-selective electrode comprising an electrode tube having opposite ends, an electrode inserted into said tube from one end thereof, an ion-selective membrane closing the other end thereof, said ion-selective membrane being selective to heparin and having a heparin diffusion rate, and a heparin-selective cross-linked polymeric coating over said other end of said tube and said membrane, said polymeric coating having a heparin diffusion rate lower than the heparin diffusion rate of said membrane.

8. An ion-selective electrode as defined in claim 7 wherein said polymeric coating comprises the reaction product of sodium dibutyl dithiocarbamate and polyvinyl chloride.

9. An ion-selective electrode of claim 7, wherein said heparin-selective cross-linked polymeric coating comprises a substituted polyvinyl chloride.

10. An ion-selective electrode of claim 7, wherein said heparin-selective cross-linked polymeric coating is substantially free of a plasticizer.

11. An ion-selective electrode comprising an electrode membrane selective to polyions and having a first diffusion rate, and a polyion-selective cross-linked polymeric coating thereon having a second diffusion rate lower than said first diffusion rate.

12. An ion-selective electrode as defined in claim 11 wherein said polymeric coating comprises a thiocarbamate-substituted polyvinyl chloride.

13. An ion-selective electrode of claim 11, wherein said polyion is a polyanion.

14. An ion-selective electrode of claim 11, wherein said polyion-selective cross-linked polymeric coating comprises a substituted polyvinyl chloride.

15. An ion-selective electrode of claim 11, wherein said heparin-selective cross-linked polymeric coating is substantially free of a plasticizer.

16. An ion-selective electrode comprising an electrode tube having opposite ends, an electrode inserted into said tube from one end thereof, an ion-selective membrane closing the other end thereof, said ion-selective membrane being selective to polyions and having a first diffusion rate, and a polyion-selective cross-linked polymeric coating over said other end of said tube and said membrane, said polymeric coating having a second diffusion rate lower than said first diffusion rate of said membrane.

17. An ion-selective electrode as defined in claim 16 wherein said polymeric coating comprises the reaction product of sodium dibutyl dithiocarbamate and polyvinyl chloride.

18. An ion-selective electrode as defined in claim 17 wherein said polymeric coating further comprises sodium dibutyl dithiocarbamate and polyvinyl chloride and a quaternary ammonium salt.

19. An ion selective electrode as defined in claim 16 wherein said polymeric coating comprises the reaction product of sodium dibutyl dithiocarbamate and polyvinyl chloride.

20. An ion-selective electrode of claim 16, wherein said polyion is a polyanion.

* * * * *